US00PP20248P3

(12) United States Plant Patent
Rogers et al.

(10) Patent No.: US PP20,248 P3
(45) Date of Patent: Sep. 1, 2009

(54) STRAWBERRY PLANT NAMED 'DRISSTRAWFIVE'

(50) Latin Name: *Fragaria×ananassa*
Varietal Denomination: DrisStrawFive

(75) Inventors: Tom Rogers, Maidstone (GB); Aloysius G Claessens, Berkel-Enschot (NL); Thomas M. Sjulin, Aromas, CA (US); Carlos D. Fear, West Malling (GB)

(73) Assignee: Driscoll Strawberry Associates, Inc., Watsonville, CA (US)

( * ) Notice: Subject to any disclaimer, the term of this patent is extended or adjusted under 35 U.S.C. 154(b) by 0 days.

(21) Appl. No.: 11/985,923

(22) Filed: Nov. 19, 2007

(65) Prior Publication Data

US 2009/0139000 P1 May 28, 2009

(51) Int. Cl.
*A01H 5/00* (2006.01)

(52) U.S. Cl. ..... Plt./209
(58) Field of Classification Search ..... Plt./209, Plt./208
See application file for complete search history.

*Primary Examiner*—S. B McCormick Ewoldt
(74) *Attorney, Agent, or Firm*—Jondle & Associates, P.C.

(57) ABSTRACT

This invention relates to a new and distinct cultivar of strawberry plant named 'DrisStrawFive'. A new cultivar primarily characterized by its small, sweet tasting fruit, moderate resistance to high pH and high soil salt levels, is disclosed.

3 Drawing Sheets

Genus and species: *Fragaria×ananassa.*
Variety denomination: 'DrisStrawFive'.

BACKGROUND OF THE NEW PLANT

The present invention relates to a new and distinct strawberry cultivar designated 'DrisStrawFive' and botanically known as *Fragaria×ananassa.* This new strawberry cultivar was discovered in Kent, England in August, 2002 and originated from a cross between the female parent 'Driscoll Jubilee' (U.S. Plant Pat. No. 15,435) and the male parent 'Driscoll Camarillo' (U.S. Plant Pat. No. 14,771). The original seedling of the new cultivar was asexually propagated at a nursery in Kent, England. 'DrisStrawFive' was subsequently asexually propagated by stolons and underwent further testing at a nursery in Monterey, Calif., for five years. The present invention has been found to retain its distinctive characteristics through successive asexual propagations by stolon.

DESCRIPTION OF THE PHOTOGRAPHS

The accompanying color photographs show typical specimens of the new cultivar at various stages of development as nearly true as it is possible to make in color reproductions.

DESCRIPTION OF THE NEW CULTIVAR

Figure 1:
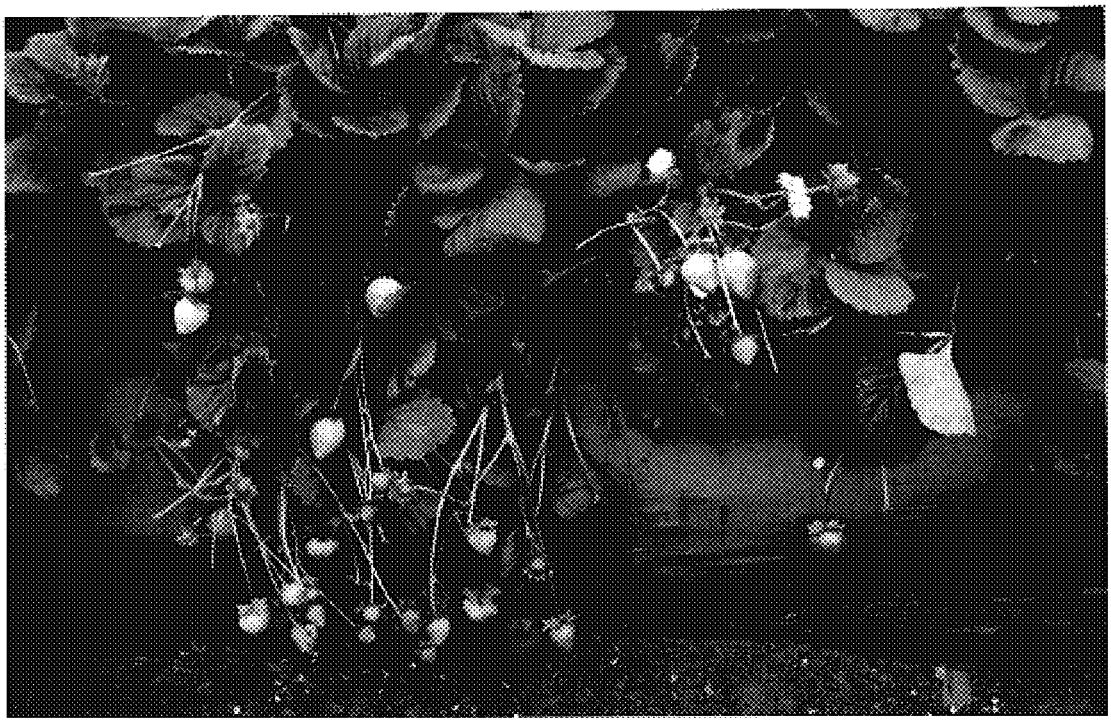
FIG. 1 shows overall plant habit including fruit at various stages of development.
Figure 2:
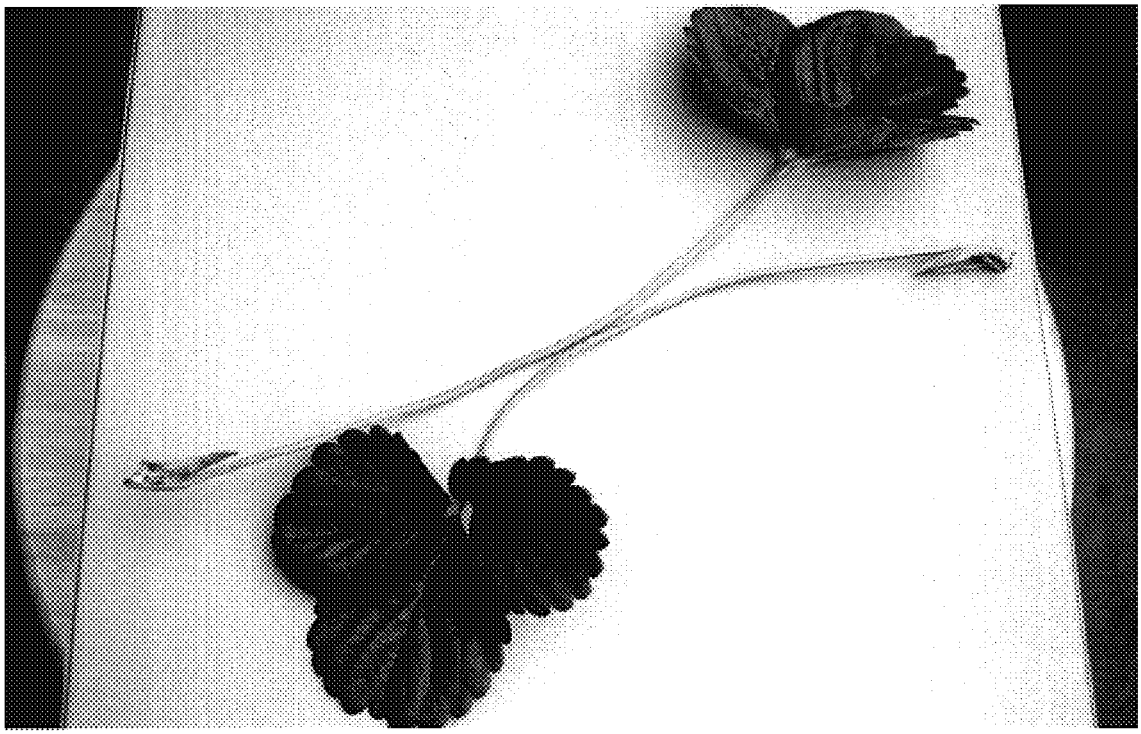
FIG. 2 shows leaves of the plant with three leaflets.
Figure 3:
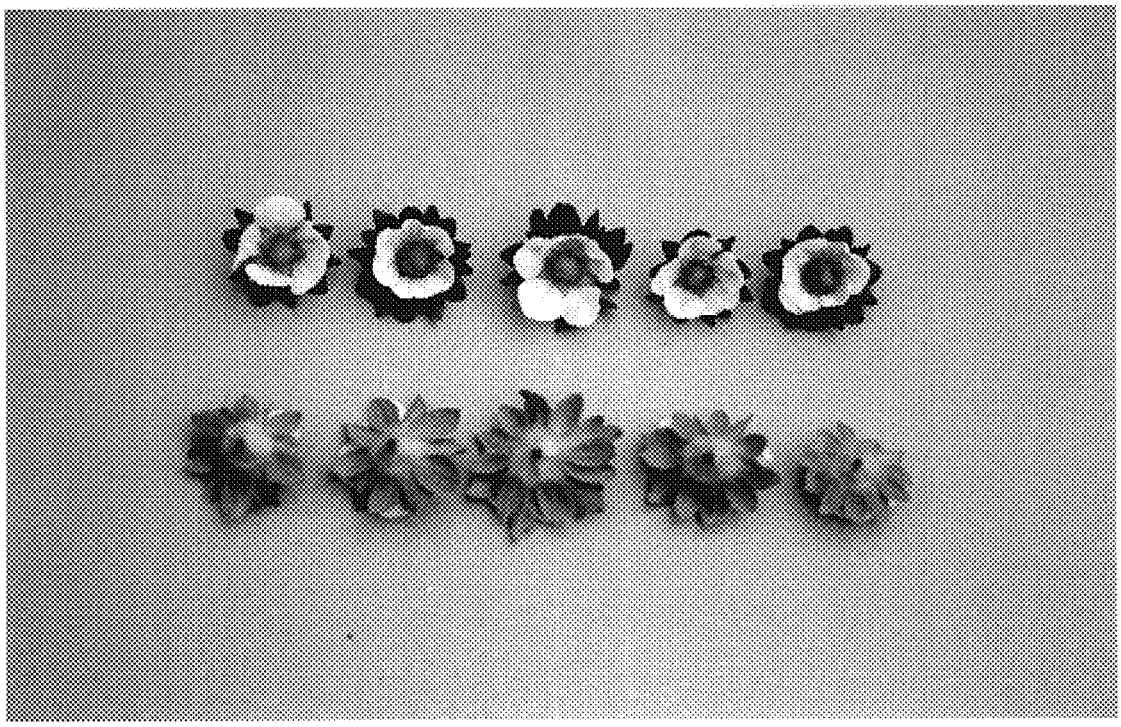
FIG. 3 shows both the upperside and underside of several of the flowers.
Figure 4:
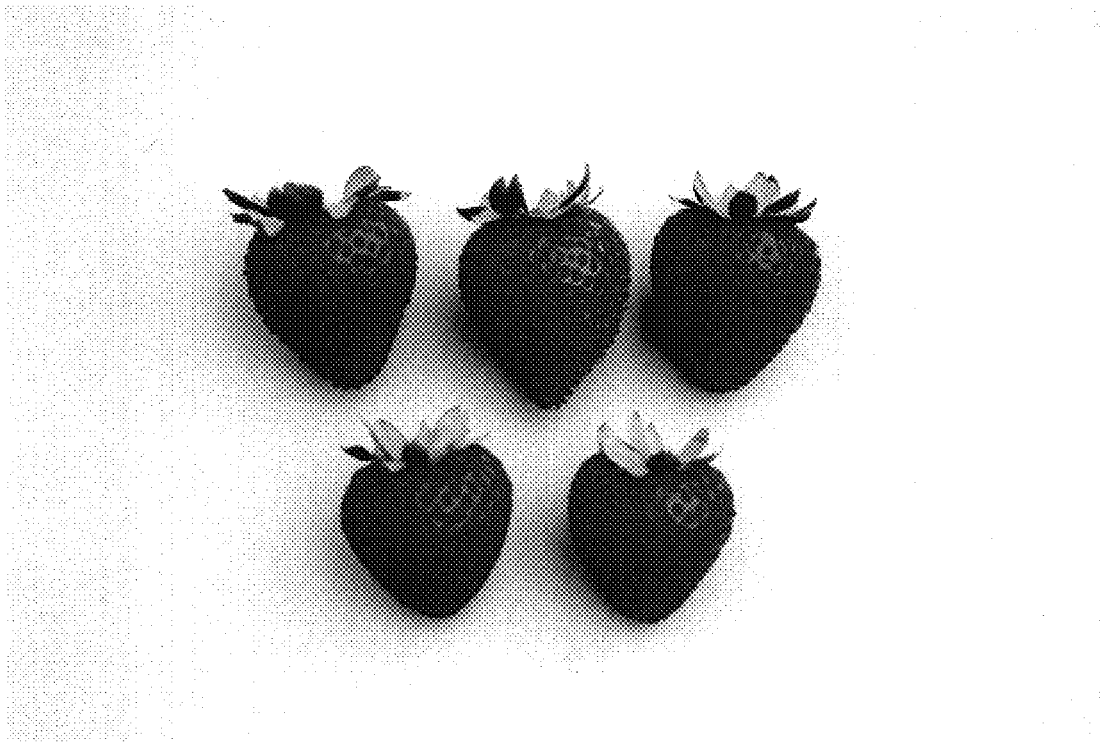
FIG. 4 shows the whole fruit.
Figure 5:
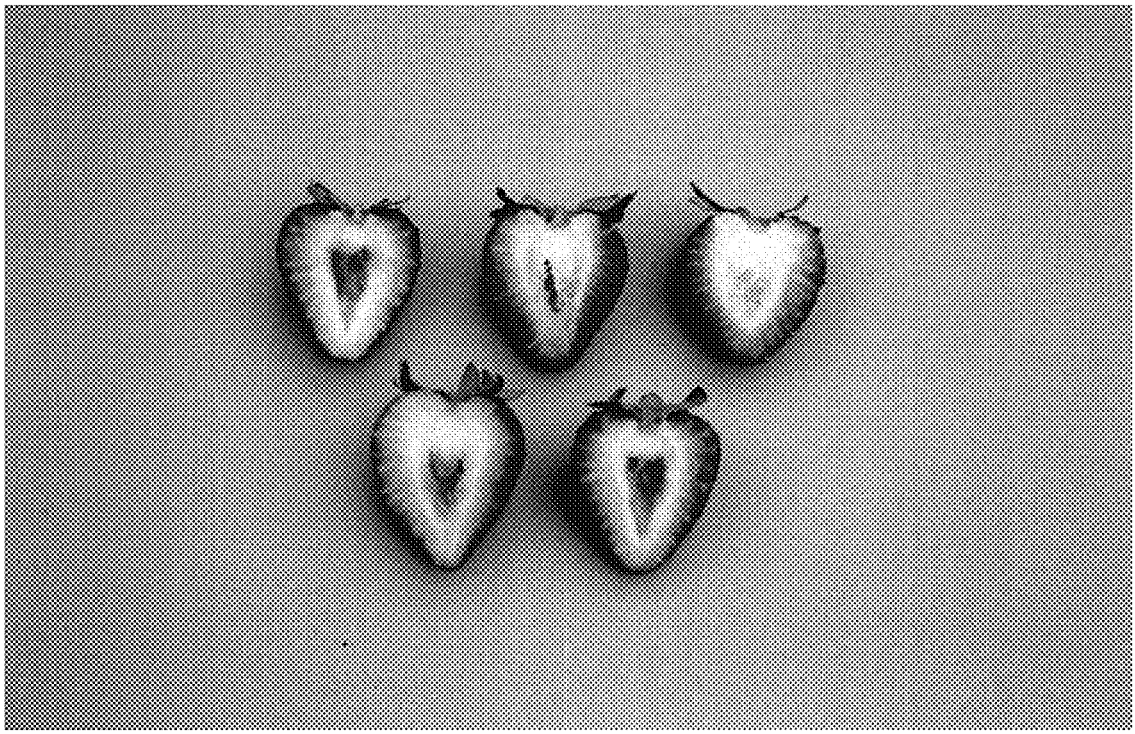
FIG. 5 shows the fruit in longitudinal cross-section.

The following description of 'DrisStrawFive' is based on observations taken from the 2002 to 2006 growing seasons in Monterey, Calif. This description is in accordance with UPOV terminology. Color designations, color descriptions, and other phenotypical descriptions may deviate from the stated values and descriptions depending upon variation in environmental, seasonal, climatic and cultural conditions. 'DrisStrawFive' has not been observed under all possible environmental conditions. Color terminology follows The Royal Horticultural Society Colour Chart, London (R.H.S.) (2001).

DETAILED BOTANICAL DESCRIPTION

Table 1 shows plant characteristics of the new variety compared with plant characteristics of the female parent 'Driscoll Jubilee' (U.S. Plant Pat. No. 15,435) and the male parent 'Driscoll Camarillo' (U.S. Plant Pat. No. 14,771). Plant characteristics include plant height, petiole length, stipule pubescence, inflorescence position relative to foliage, flower size, diameter of calyx relative to corolla, fruit truss length, and fruit size.

TABLE 1

| Characteristic | 'DrisStrawFive' | 'Driscoll Jubilee' | 'Driscoll Camarillo' |
|---|---|---|---|
| Plant height (cm) | 31.2 | 25.7 | 27.2 |
| Petiole length (cm) | 22.2 | 16.3 | 16.8 |
| Stipule pubescence | Dense | Between sparse and medium | Sparse |
| Inflorescence position relative to foliage | Between level with and above | Beneath | Above |
| Flower size | Small | Between small and medium | Medium |
| Diameter of calyx relative to corolla | Between same size and larger | Between smaller and same size | Between smaller and same size |
| Fruit truss length (cm) | 31.7 | 19.6 | 27.6 |
| Fruit size | Small | Between small and medium | Between medium and large |

Table 2 shows plant characteristics of the new variety compared with plant characteristics of the commercial varieties 'Driscoll Jubilee' (U.S. Plant Pat. No. 15,435) and 'Driscoll Camarillo' (U.S. Plant Pat. No. 14,771). Plant characteristics include plant height, diameter, number of crowns per plant, habit, density of individual plant and vigor.

TABLE 2

| Characteristic | 'DrisStrawFive' | 'Driscoll Jubilee' | 'Driscoll Camarillo' |
|---|---|---|---|
| Plant height (cm) | 31.2 | 25.7 | 27.2 |
| Plant diameter (cm) | 50.0 | 44.5 | 49.7 |
| Number of crowns/plant | 4 | 4 | 5 |
| Habit | Globose | Flat globose | Globose |
| Density of individual plant | Medium | Between open and medium | Open |
| Vigor | Strong | Between weak and medium | Medium |

Table 3 shows leaf characteristics of the new cultivar compared with leaf characteristics of 'Driscoll Jubilee' and 'Driscoll Camarillo'. Leaf characteristics include terminal leaflet length and width in centimeters, length to width ratio, number of teeth per terminal leaflet, shape of teeth, color of upperside and underside of leaf, leaf shape in cross section, leaf blistering, leaf glossiness, number of leaflets, terminal leaflet margin, terminal leaflet length to width ratio and shape of leaf base.

TABLE 3

| Leaf Characteristic | 'DrisStrawFive' | 'Driscoll Jubilee' | 'Driscoll Camarillo' |
|---|---|---|---|
| Terminal leaflet length (cm) | 0.72 | 0.75 | 0.71 |
| Terminal leaflet width (cm) | 0.66 | 0.68 | 0.75 |
| Terminal leaflet length/width ratio | 1.09 | 1.10 | 0.95 |
| No. teeth/terminal leaflet | 17 | 18 | 23 |
| Shape of teeth | Rounded | Rounded | Rounded |
| Color of upperside of leaf | RHS 139A Dark green | RHS 147A Dark yellow-green | RHS 147A Dark yellow-green |
| Color of underside of leaf | RHS N138C Medium greyed-green | RHS 138B Medium green | RHS 138B Medium green |
| Leaf shape in cross section | Flat | Between slightly concave and flat | Concave |
| Leaf blistering | Strong | Strong | Very strong |
| Leaf glossiness | Weak | Medium | Between medium and strong |
| No. leaflets | Three only | Three only | Three only |
| Terminal leaflet margin | Revolute | Revolute | Between revolute and flat |
| Terminal leaflet: length/width ratio | Between as long as broad and longer than broad | Between as long as broad and longer than broad | Between broader than long and as long as broad |
| Terminal leaflet base shape | Rounded | Acute | Rounded |

Table 4 shows information about the petiole, the petiolule, the bract, and the stipule of the new cultivar compared to 'Driscoll Jubilee' and 'Driscoll Camarillo'. This includes petiole length in centimeters, petiole diameter in centimeters, petiole pubescence, pose of hairs on the petiole, color of the petiol, color of the petiolule, petiolule length in centimeters, petiolule diameter in centimeters, bract frequency per petiole, stipule length in centimeters, stipule width in centimeters, and stipule pubescence.

TABLE 4

| Characteristic | 'DrisStrawFive' | 'Driscoll Jubilee' | 'Driscoll Camarillo' |
|---|---|---|---|
| Petiole length (cm) | 22.2 | 16.3 | 16.8 |
| Petiole diameter (cm) | 0.256 | 0.354 | 0.331 |
| Petiole pubescence | Dense | Absent or very sparse | Sparse |
| Petiole pose of hairs | Outward | Between outward and downward | Outward |
| Petiole color | RHS 145A Light yellow-green | RHS 145A Light yellow-green | RHS 149A Bright yellow-green |
| Petiolule color | RHS 144A Medium yellow-green | RHS 146C Dark yellow-green | RHS 144B Medium yellow- green |
| Petiolule length (cm) | 1.004 | 1.172 | 1.373 |
| Petiolule diameter (cm) | 0.156 | 0.181 | 0.194 |
| Bract frequency | 0 | 0 | 0 |
| Stipule length (cm) | 3.5 | 3.4 | 4.0 |
| Stipule width (cm) | 0.765 | 0.978 | 0.866 |
| Stipule pubescence | Dense | Between sparse and medium | Sparse |

Table 5 shows stolon characteristics of the new cultivar compared to 'Driscoll Jubilee' and 'Driscoll Camarillo'. These characteristics include the number of stolons, average number of daughter plants, the anthocyanin coloration of the stolons, the thickness of the stolons, and the pubescence of the stolons.

TABLE 5

| Characteristic | 'DrisStrawFive' | 'Driscoll Jubilee' | 'Driscoll Camarillo' |
|---|---|---|---|
| Stolon Number | Medium | Medium | Medium |
| Average number of daughter plants | 13 | 45 | 40 |
| Stolon Anthocyanin | Strong RHS 59D Medium Red-purple | Medium | Medium |
| Stolon Thickness | Thin | Between thin and medium | Between medium and thick |
| Stolon Pubescence | Sparse | Between sparse and medium | Medium |

Table 6 shows inflorescence characteristics of the new cultivar compared to 'Driscoll Jubilee' and 'Driscoll Camarillo'. These characteristics include inflorescence position relative to foliage, relative flower size, flower diameter in centimeters (measured from petal tip to petal tip), relative spacing of petals, petal length in centimeters, petal width in centimeters, petal length to width ratio, petal color, calyx diameter in centimeters (measured on back of flower from sepal tip to sepal tip), diameter of calyx relative to corolla, diameter of inner calyx relative to outer, sepal length in centimeters (measured from sepal tip to point of attachment to receptacle), sepal width in centimeters, receptacle color and anther color.

TABLE 6

| Characteristic | 'DrisStrawFive' | 'Driscoll Jubilee' | 'Driscoll Camarillo' |
|---|---|---|---|
| Inflorescence position relative to foliage | Between level with and above | Beneath | Above |
| Flower size | Small | Between small and medium | Medium |
| Flower diameter (cm) | 2.174 | 2.299 | 2.698 |
| Petal spacing | Overlapping | Between touching and overlapping | Overlapping |
| Petal length (cm) | 1.054 | 1.192 | 1.275 |
| Petal width (cm) | 1.035 | 1 142 | 1.367 |
| Petal length/width ratio | As long as broad | As long as broad | Between broader than long and as long as broad |
| Petal length/width ratio | 1.02 | 1.04 | 0.93 |
| Petal color | RHS 155C White | RHS 155C White | RHS 155B White |
| Calyx diameter (cm) | 2.726 | 2.910 | 3.233 |
| Calyx diameter relative to corolla | Between same size and larger | Between smaller and same size | Between smaller and same size |
| Inner calyx diameter relative to outer | Larger | Smaller | Same size |
| Sepal length (cm) | 0.957 | 1.098 | 1.118 |
| Sepal width (cm) | 0.626 | 0.540 | 0.709 |
| Receptacle color | RHS 1B Bright green-yellow | RHS 1B Bright green-yellow | RHS 1A Bright green-yellow |
| Anther color | RHS 23A Bright yellow-orange | RHS 23A Bright yellow-orange | RHS 17A Dull yellow-orange |

Table 7 shows fruit characteristics of the new cultivar compared to 'Driscoll Jubilee' and 'Driscoll Camarillo'. These characteristics include fruiting truss length in centimeters, fruiting truss attitude, fruiting truss length, fruit length in centimeters, fruit truss width in centimeters, fruit length to width ratio, fruit weight in grams, relative fruit size, predominant fruit shape, difference in shape between primary and secondary fruits, band without achenes, unevenness of fruit surface, fruit skin color, evenness of fruit color, fruit glossiness, insertion of achenes, achene coloration (sunward and shaded sides of berry), achenes per berry, achene weight in grams, insertion of calyx, pose of calyx segments, size of calyx in relation to fruit, adherence of calyx, firmness of flesh, color of the fruit flesh, evenness of the flesh color, distribution of flesh color, hollow center, sweetness of fruit, acidity of fruit, texture of fruit when tasted, time of flowering, harvest maturity, type of bearing, grams of fruit per plant.

TABLE 7

| Characteristic | 'DrisStrawFive' | 'Driscoll Jubilee' | 'Driscoll Camarillo' |
|---|---|---|---|
| Fruiting truss length (cm) | 31.7 | 19.6 | 27.6 |
| Fruiting truss attitude | Semi-erect | Semi-erect | Prostrate |
| Fruiting truss length | Long | Medium | Long |
| Fruit length (cm) | 3.52 | 3.59 | 3.59 |

TABLE 7-continued

| Characteristic | 'DrisStrawFive' | 'Driscoll Jubilee' | 'Driscoll Camarillo' |
|---|---|---|---|
| Fruit width (cm) | 3.28 | 3.07 | 3.29 |
| Fruit length/width ratio | 1.07 | 1.17 | 1.09 |
| Fruit length/width ratio | Between as long as broad and longer than broad | Longer than broad | Between as long as broad and longer than broad |
| Fruit weight (g) | 19.4 | 17.3 | 20.6 |
| Relative fruit size | Small | Between small and medium | Between medium and large |
| Predominant fruit shape | Conical | Conical | Cordate |
| Difference in shape between primary & secondary fruits | None or very slight | Between none or very slight and slight | Slight |
| Band without achenes | Absent or very narrow | Absent or very narrow | Absent or very narrow |
| Unevenness of fruit surface | Absent or very weak | Absent or very weak | Weak |
| Fruit skin color | RHS 45A Bright red | RHS 45A Bright red | RHS 46A Dark red |
| Evenness of fruit color | Even | Slightly uneven | Even |
| Fruit glossiness | Strong | Strong | Strong |
| Insertion of achenes | Level with surface | Between level with surface and above surface | Below surface |
| Achene coloration-sunward side of berry | RHS 185A Medium greyed-purple | RHS 184A Medium greyed-purple | RHS 184A Medium greyed-purple |
| Achene coloration-shaded side of berry | RHS 7D Medium yellow | RHS 4A Bright medium yellow | RHS 13B Medium orange-yellow |
| Achenes per berry | 164.6 | 131.3 | 224.0 |
| Achene weight (grams) | 0.000499453 | 0.000616527 | 0.000626027 |
| Insertion of calyx | Level | Between in a basin and level | In a basin |
| Pose of calyx segments | Between spreading and reflexed | Spreading | Reflexed |
| Size of calyx in relation to fruit | Between same size and larger | Between smaller and same size | Smaller |
| Adherence of calyx | Strong | Strong | Strong |
| Firmness of flesh | Firm | Between medium and firm | Firm |
| Color of the flesh | RHS 155D White and RHS 41C Very light red | RHS 43A Bright red and RHS 155B White | RHS 34B Medium orange red and RHS 155A White |
| Evenness of flesh color | Uneven | Slightly uneven | Slightly uneven |
| Distribution of flesh color | Only marginal | Marginal and central | Marginal and central |
| Hollow center | Between absent and small | Between absent and small | Between absent and small |
| Sweetness | Between medium and strong | Between medium and strong | Medium |
| Acidity | Medium | Medium | Medium |
| Texture when tasted | Medium | Medium | Medium |
| Time of flowering | Medium | Medium | Medium |
| Harvest maturity (50% of plants with ripe fruit) | Late April to early November | Early May to late October | Late September to late December |

TABLE 7-continued

| Characteristic | 'DrisStrawFive' | 'Driscoll Jubilee' | 'Driscoll Camarillo' |
|---|---|---|---|
| Type of bearing | Fully everbearing | Fully everbearing | Fully everbearing |
| Grams of fruit/plant | 518 | 979 | 1,485 |

Table 8 shows the resistance to different forms of stress of the new cultivar compared to 'Driscoll Jubilee' and 'Driscoll Camarillo'. These forms of stress include high pH and high soil salt levels.

TABLE 8

| Reaction to Stress | 'DrisStrawFive' | 'Driscoll Jubilee' | 'Driscoll Camarillo' |
|---|---|---|---|
| High pH | Moderately resistant | Moderately resistant | Moderately resistant |
| High soil salt levels | Moderately resistant | Moderately susceptible | Moderately resistant |

Table 9 shows pest and disease characteristics of the new cultivar compared to 'Driscoll Jubilee' and 'Driscoll Camarillo'.

TABLE 9

| Pest or Disease | 'DrisStrawFive' | 'Driscoll Jubilee' | 'Driscoll Camarillo' |
|---|---|---|---|
| *Tetranychus urticae* (2-spotted spider mite) | Moderately susceptible | Moderately susceptible | Moderately susceptible |
| *Tarsonemus pallidus* | Susceptible | Susceptible | Susceptible |
| Botrytis fruit rot | Moderately resistant to moderately susceptible | Moderately resistant to moderately susceptible | Moderately resistant to moderately susceptible |
| Powdery mildew | Susceptible | Susceptible | Between susceptible and highly susceptible |
| Verticillium wilt | Moderately resistant to moderately susceptible | Moderately resistant | Moderately susceptible |

Table 10 shows overall characteristics of the new cultivar compared to 'DrisStrawOne' (U.S. Plant Pat. No. 18,458). These characteristics include the plant height and diameter in centimeters, petiole length and diameter in centimeters, fruit length and width in centimeters; fruit sweetness and fruit texture when tasted.

TABLE 10

| Characteristic | 'DrisStrawFive' | 'DrisStrawOne' |
|---|---|---|
| Height (cm) | 31.2 | 9.5 |
| Diameter (cm) | 50.0 | 15.9 |
| Petiole length (cm) | 22.2 | 12.5 |
| Petiole diameter (cm) | 0.256 | 0.385 |
| Fruit length (cm) | 3.52 | 0.538 |
| Fruit width (cm) | 3.28 | 0.452 |
| Sweetness | Between medium and strong | Medium |
| Texture when tasted | Medium | Fine |

We claim:

1. A new and distinct cultivar of strawberry plant as described and shown herein.

* * * * *